(12) United States Patent
Peyman et al.

(10) Patent No.: US 11,744,617 B2
(45) Date of Patent: Sep. 5, 2023

(54) NON-INVASIVELY ADJUSTABLE SPINAL STABILIZATION DEVICE

(71) Applicants: Nazmi Peyman, Richmond, VA (US); Edmond Zahedi, Burnaby (CA)

(72) Inventors: Nazmi Peyman, Richmond, VA (US); Edmond Zahedi, Burnaby (CA)

( * ) Notice: Subject to any disclaimer, the term of this patent is extended or adjusted under 35 U.S.C. 154(b) by 0 days.

(21) Appl. No.: 17/500,770

(22) Filed: Oct. 13, 2021

(65) Prior Publication Data
US 2022/0110660 A1 Apr. 14, 2022

Related U.S. Application Data

(60) Provisional application No. 63/090,959, filed on Oct. 13, 2020.

(51) Int. Cl.
*A61B 17/70* (2006.01)
*A61B 17/00* (2006.01)

(52) U.S. Cl.
CPC ............... *A61B 17/7016* (2013.01); *A61B 2017/00221* (2013.01); *A61B 2017/00477* (2013.01); *A61B 2017/00876* (2013.01)

(58) Field of Classification Search
CPC .................................. A61B 17/7001–7031
See application file for complete search history.

(56) References Cited

U.S. PATENT DOCUMENTS

| | | | |
|---|---|---|---|
| 5,810,815 A * | 9/1998 | Morales | A61B 17/7055 606/261 |
| 9,339,298 B1 * | 5/2016 | Morales Chavarria | A61B 17/7023 |
| 2014/0222074 A1 * | 8/2014 | Rathbun | A61B 17/705 606/258 |
| 2014/0296918 A1 * | 10/2014 | Fening | A61B 17/707 29/428 |
| 2015/0119939 A1 * | 4/2015 | Frey | A61B 17/7031 606/258 |
| 2015/0190175 A1 * | 7/2015 | Oldakowski | A61B 17/7007 606/246 |

(Continued)

*Primary Examiner* — Eduardo C Robert
*Assistant Examiner* — Steven J Cotroneo
(74) *Attorney, Agent, or Firm* — Barry Choobin; Patent 360

(57) ABSTRACT

A spinal stabilization device that can be used to non-invasively correct spacing and curvature between at least two vertebral structures. The spinal stabilization device includes two telescoping tubes wherein ends of the two tubes can have pedicle screws that can be fastened to two or more vertebral bones. The overall length of the spinal stabilization device can be adjusted by moving the inner tube within the outer tube. Both the outer tube and the inner tube have multiple holes for receiving fasteners, wherein a fastener can be inserted through a hole in the outer tube into a hole in the inner tube for interlocking the inner tube and outer tube. The extension of the fastener into the holes and retraction from the holes can be controlled non-invasively from an external source. When the fastener is disengaged, the inner tube and the outer tube can freely move relative to each other, and the positions of the two or more vertebral bones can be non-invasively adjusted by subjecting a person to predefined movements and body posture. Upon achieving the desired positions, the fastener can be engaged to interlock the inner tube and the outer tube.

17 Claims, 11 Drawing Sheets

(56) References Cited

U.S. PATENT DOCUMENTS

| | | | |
|---|---|---|---|
| 2015/0335358 A1* | 11/2015 | Luhmann | A61B 17/7014 |
| | | | 606/279 |
| 2017/0231661 A1* | 8/2017 | Bannigan | A61B 17/7043 |
| | | | 606/263 |
| 2017/0231663 A1* | 8/2017 | Hammann | A61B 17/7016 |
| | | | 606/258 |
| 2017/0265900 A1* | 9/2017 | Lai | A61B 17/7014 |
| 2018/0125533 A1* | 5/2018 | Arnin | A61B 17/7071 |
| 2019/0269438 A1* | 9/2019 | Simpson | A61B 17/7017 |
| 2019/0282277 A1* | 9/2019 | Arnin | A61B 17/7014 |
| 2020/0030003 A1* | 1/2020 | Charest | A61B 17/7016 |
| 2022/0008102 A1* | 1/2022 | Charest | A61B 17/7014 |

\* cited by examiner

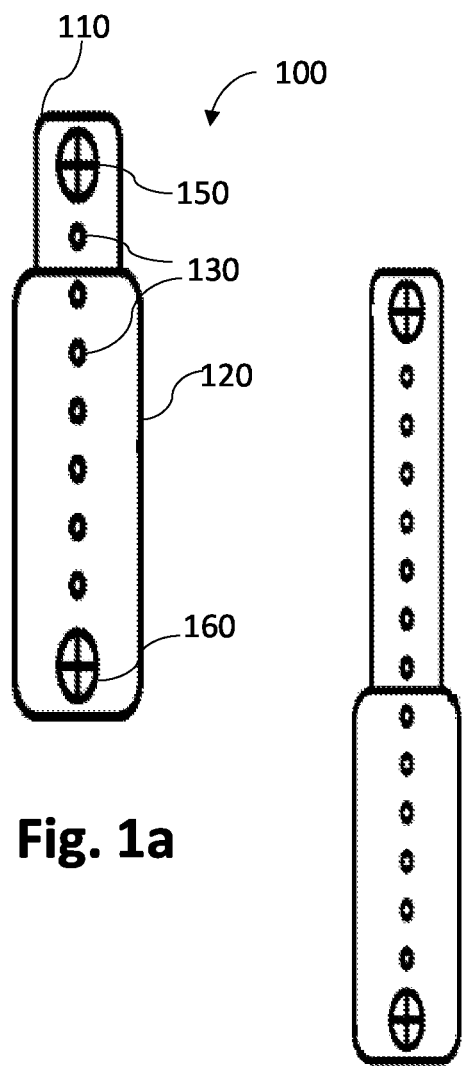
Fig. 1a
Fig. 1b
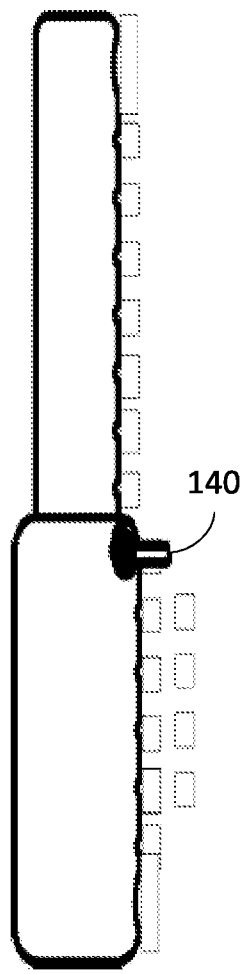
Fig. 1c

NON-INVASIVELY ADJUSTABLE SPINAL STABILIZATION DEVICE

CROSS-REFERENCE TO RELATED APPLICATIONS

This application claims priority from the U.S. provisional patent application Ser. No. 63/090,959, filed on Oct. 13, 2020, which is incorporated herein by reference in its entirety.

FIELD OF INVENTION

The present invention relates to a spinal stabilization device, and more particularly, the present invention relates to a telescoping device that can be anchored to two or more vertebral structures.

BACKGROUND

Degenerative changes of the spinal structures, such as intervertebral discs and facet joints can cause significant degrees of bodily pains, in particular, pain in the spine, legs, and arms. Spinal stenosis is a common problem caused by narrowing of the spaces within the spinal canal, putting extra pressure on the spinal cord and spinal nerves. Spinal stenosis is a leading cause of lower back pains. Various factors, in particular increased age, sedentary lifestyle, or trauma are responsible for various degrees of spinal degeneration.

The primary treatment for spinal degenerative disorders is medication and physical therapy which tend to provide relief from the pain and strengthen the muscles. Surgery is needed in cases unresponsive to the primary treatment using medicines and physical therapy. Through surgery, the natural spacing between the vertebral bones can be restored allowing for the release of the pinching of the nerves.

Spinal fixation instruments and fusion surgeries are commonly used for a variety of spinal conditions including spinal stenosis, spondylosis, and unstable spine. However, spinal surgery is not always successful and often patients report a significant degree of pain after the surgery. Studies reporting up to 50 percent of the patients undergone spinal surgery reports recurrent pain and other complications are not uncommon?

One of the reasons for post-surgery complications is that the surgery is performed with the patient under complete sedation or general anesthesia and in the prone and fully relaxed body position. After the surgery, when the patient engages in any physical activity, such as standing and walking, the position and angle of curvatures of the spine change. Upon the resulting activity after surgery, if the curvatures of the spine are not natural, it may potentially cause additional pain and discomfort. Furthermore, even when the spine is fused in an optimum shape, curvature, and position during the surgery, over the long run, there may be more wear and tear and/or degeneration of tissues and spine, leading to pain and other medical conditions. A need, therefore, arises to readjust the position of the spinal instrumentation. With the present technology, once the instrumentation is in place, it is not possible to modify its configuration without surgery. Hence another and more complicated surgery is required. This surgery may even be repeated a third or more times.

Thus, a desire is there for a versatile device that can be adjusted and readjusted non-invasively post-surgery according to the needs of a patient, thus preventing the need for subsequent invasive surgeries.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a spinal stabilization device that can be non-invasively reconfigured post-surgery.

It is another object of the present invention that the spinal stabilization device prevents the need for a subsequent invasive surgery to reconfigure the spinal implementation.

It is yet another object of the present invention that the spinal stabilization device reduces the effective duration of treatment by preventing the need for multiple invasive surgeries.

It is still a further object of the present invention that the spinal stabilization device reduces the overall cost of the treatment.

In one aspect, disclosed is a spinal stabilization device that can be used to correct spacing and angle between two or more vertebral structures. The disclosed stabilization device can include two telescoping tubes wherein the ends of the two telescoping tubes can have pedicle screws. It is understood that more than two telescoping tubes are within the scope of the present invention. For example, an upper tube, a middle tube, and a lower tube, wherein the middle tube is slidably received in the lower tube and the upper tube is slidably received in the middle tube, however multiple telescoping tubes can be arranged in any other manner and any such arrangement of the telescoping tubes is within the scope of the present invention. The two telescoping tubes can be coupled to the respective at least two vertebral bones using the pedicle screws. The overall length of the spinal stabilization device can be adjusted by moving the inner tube within the outer tube. The device can further include one or more fasteners and a fastener casing, wherein the fastener can be used to interlock the inner tube and the outer tube, preventing any further movement of the inner tube and at the desired length.

In one aspect, the fastener can be actuated by an external source non-invasively from outside the body through intact skin to engage and disengage the fastener.

In one aspect, the inner and outer tubes can have multiple corresponding holes and the fastener can be a pin that can be inserted through a hole in the outer tubes into a hole in the inner tube restricting the movement of the inner tube. Optionally more than one pin can be provided that can be inserted in more than one hole simultaneously for additional strength.

These and other objects and advantages of the embodiments herein and the summary will become readily apparent from the following detailed description taken in conjunction with the accompanying drawings.

BRIEF DESCRIPTION OF THE DRAWINGS

The accompanying figures, which are incorporated herein, form part of the specification and illustrate embodiments of the present invention. Together with the description, the figures further explain the principles of the present invention and are meant to enable a person skilled in the relevant arts to make and use the invention.

FIG. 1a shows a spinal stabilization device including two telescoping tubes, i.e., an inner tube and an outer tube, according to an exemplary embodiment of the present invention.

FIG. 1b shows the spinal stabilization device as in FIG. 1a with the inner tube fully extended, according to an exemplary embodiment of the present invention.

FIG. 1c shows a side view of the spinal stabilization device as in FIG. 1b, according to an exemplary embodiment of the present invention.

DETAILED DESCRIPTION

Figure 2:
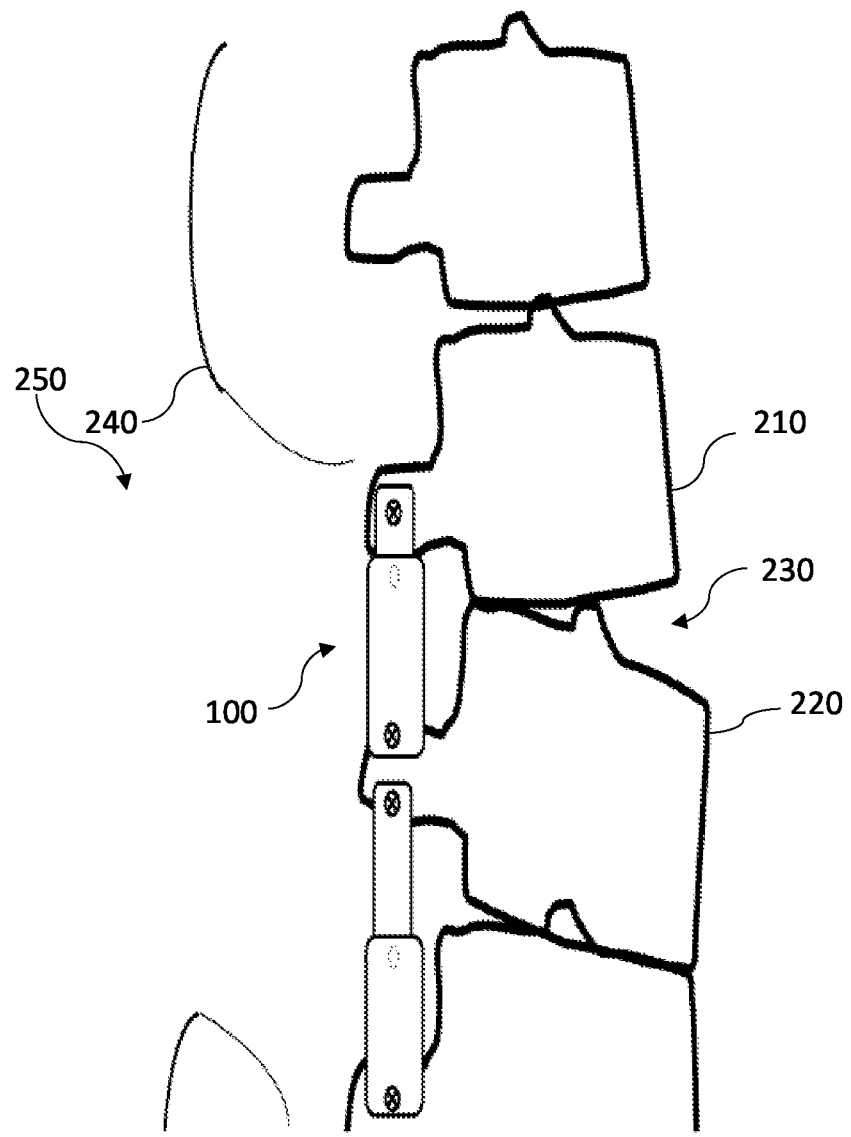
FIG. 2 shows the spinal stabilization device implanted to two adjacent vertebral bones, using an invasive surgery including an incision in the skin, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a device for spinal stabilization and a method of use thereof. The device can be anchored to two or more vertebral structures, such as vertebra or bones. The disclosed spinal stabilization device can be used to restore spacing and angle (curvature) between two or more vertebral structures to or close to the natural spacing and curvature. The spinal stabilization system can rigidly support the two or more vertebral structures at the desired spacing. The use of plates and anchors is known in the art to support two or more bone structures. The disclosed spinal stabilization device is advantageous by permitting to change the length and curvature of the device non-invasively.

Referring to FIG. 1a which shows an exemplary embodiment of the spinal stabilization device 100 that includes an inner tube 110 and an outer tube 120. Both the inner tube and the outer tube can be made from strong, rigid, and medical-grade material. The inner tube can slide within the outer tube, wherein the length of the spinal stabilization device 100 can be increased by drawing out the inner tube and the length of the spinal stabilization device 100 can be decreased by sliding in the inner tube into the outer tube. Both the inner tube 110 and the outer tube 120 can have multiple holes 130 along the length of the inner tube 110 and the outer tube 120. The position of holes in the outer tube 120 can correspond to the positions of the holes in the inner tube 110, such as a fastener can be inserted through a hole in the outer tube 120 into a hole in the inner tube 110, thereby restricting the movement of the inner tube relative to the outer tube. FIG. 1a shows the majority of the inner tube 110 inserted into the outer tube 120. FIG. 1b shows the majority of the inner tube 110 extended out from the outer tube 120. FIG. 1c is a side view of the spinal stabilization device 100 showing the pin 140 that can be inserted into the holes 130. More than one fastener can be used that can be inserted into more than one hole of the outer tube into respective holes of the inner tube for additional strength. Each the inner tube 110 and the outer tube 120 can have a proximal end and a distal end. The proximal end of the inner tube can be inserted into the distal end of the outer tube. The distal end of the inner tube can have a first pedicle screw 150 and the proximal end of the outer tube can have a second pedicle screw 160. Both the first pedicle screw 150 and the second pedicle screw 160 can be anchored to the vertebral bones for securing the spinal stabilization device 100. The structure and functioning of the pedicle screws are known in the art and any such pedicle screw is within the scope of the present invention.

Referring to FIG. 2 which shows the disclosed spinal stabilization device 100 anchored to a first vertebral bone 210 and a second vertebral bone 220, wherein the first vertebral bone 210 and the second vertebral bone 220 are adjacent to each other. The spacing 230 between the first vertebral bone 210 and the second vertebral bone 220 needs to be adjusted, explaining why the vertebrae 210 and 220 are shown disoriented. The spinal stabilization device 100 can be implanted through invasive surgery. FIG. 2 shows skin 240 and an incision 250 in the skin 240 made for implanting the spinal stabilization device 100. The spinal stabilization device 100 can be installed before the inter-vertebral space adjustment. Moreover, the fastener or pins are disengaged that may allow the inner tube 110 to freely move within the outer tube.

Figure 3:
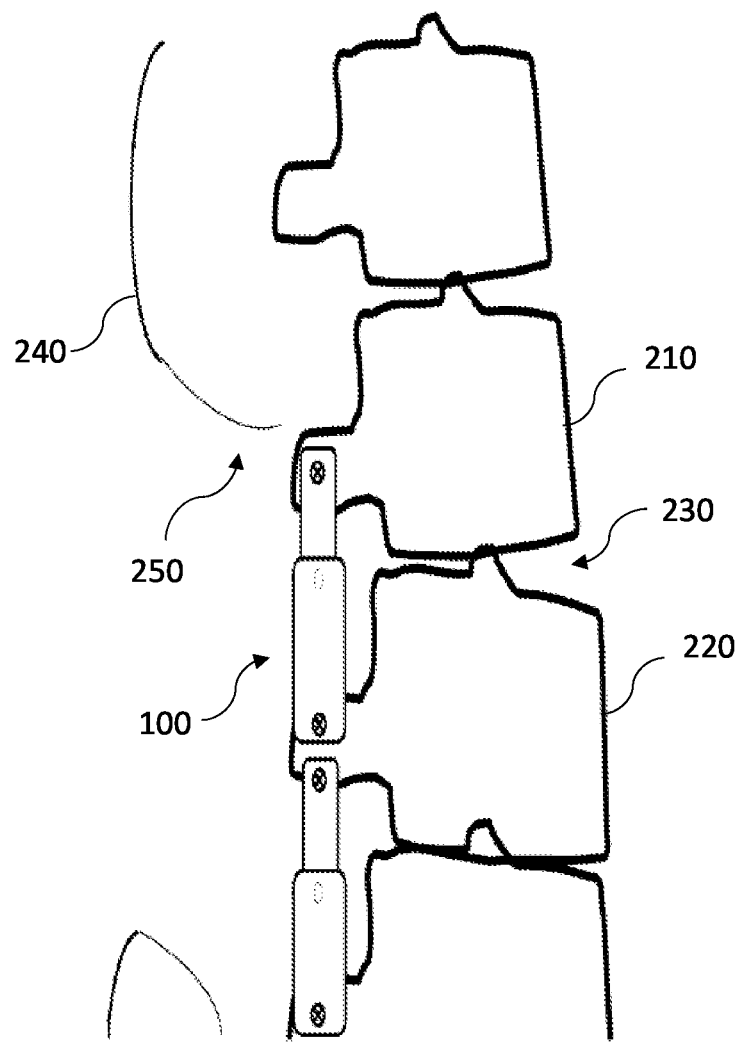
FIG. 3 shows the spinal stabilization device as in claim 2 but after adjusting the spacing between the successive vertebral bones and interlocking the inner tube and the outer tube, according to an exemplary embodiment of the present invention.
Figure 4:
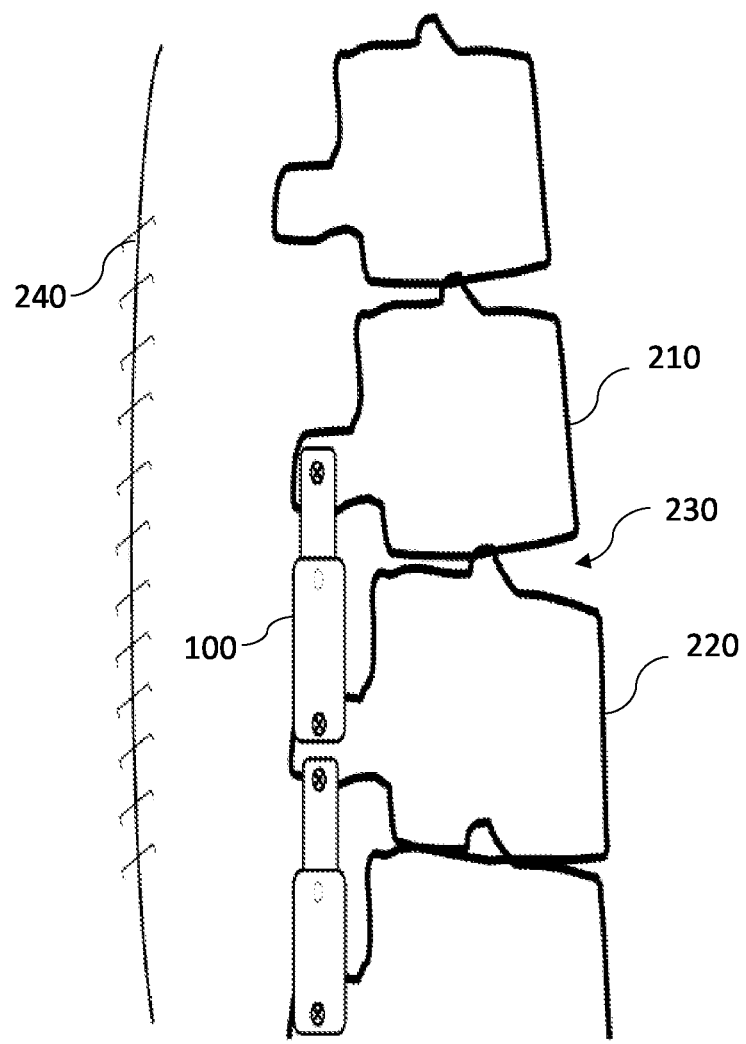
FIG. 4 depicts an exemplary embodiment of the spinal stabilization device fixed to two successive vertebral bones after surgery and skin joined, according to an exemplary embodiment of the present invention.
Figure 5:
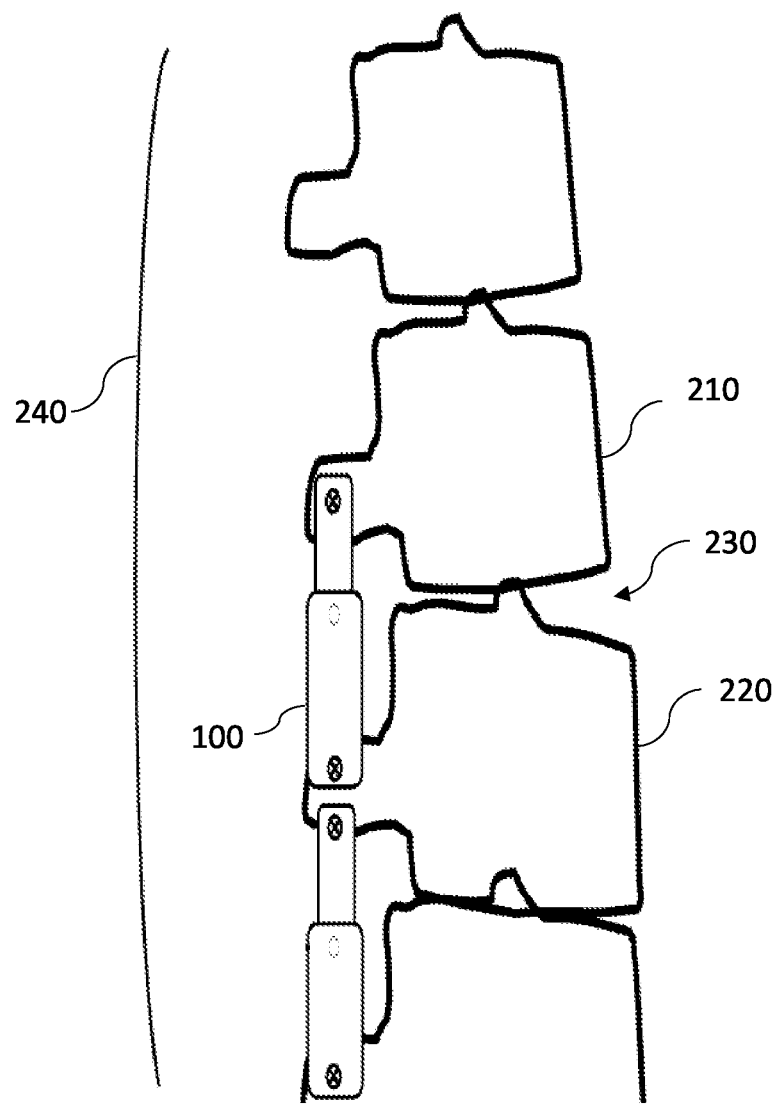
FIG. 5 depicts the spinal stabilization device fixed to the two successive vertebral bones after healing of the incision made during surgery, according to an exemplary embodiment of the present invention.
Figure 6:
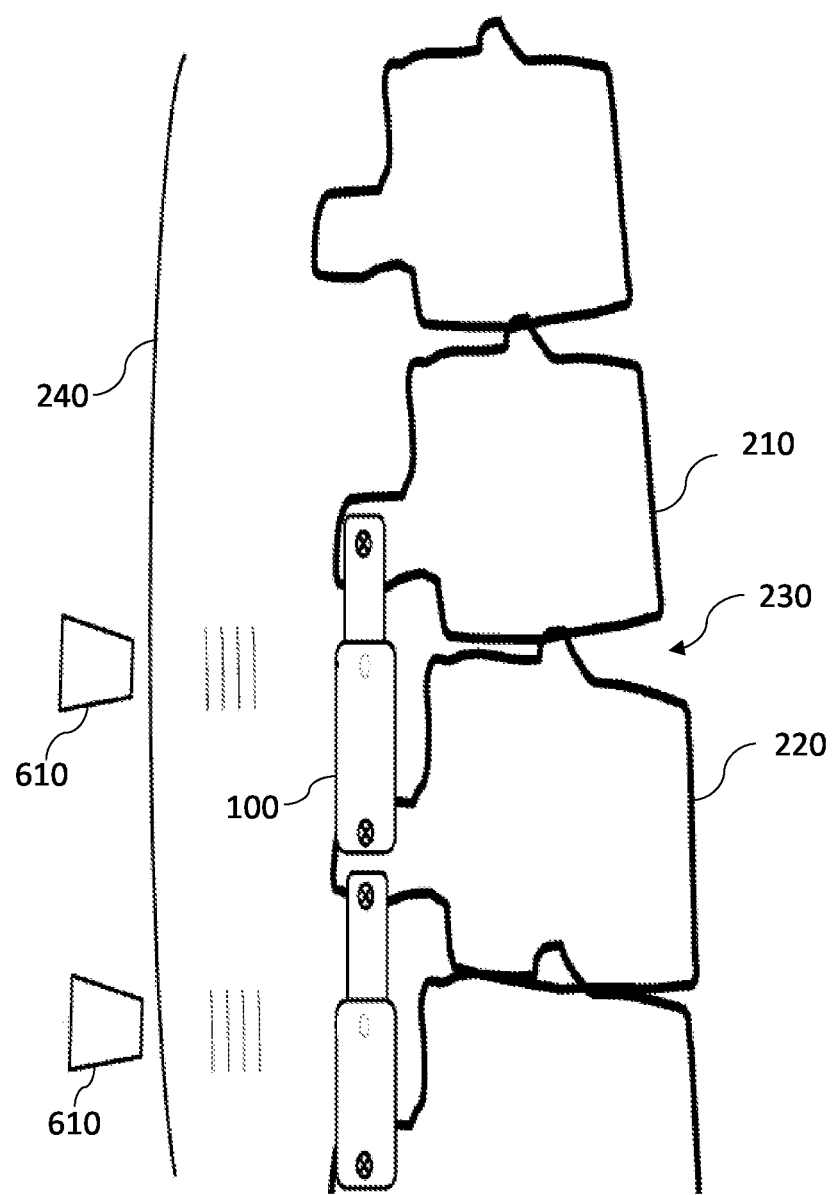
FIG. 6 depicts an application of an external magnetic field to disengage a fastener pin (after healing) from the spinal stabilization device, according to an exemplary embodiment of the present invention.
Figure 7:
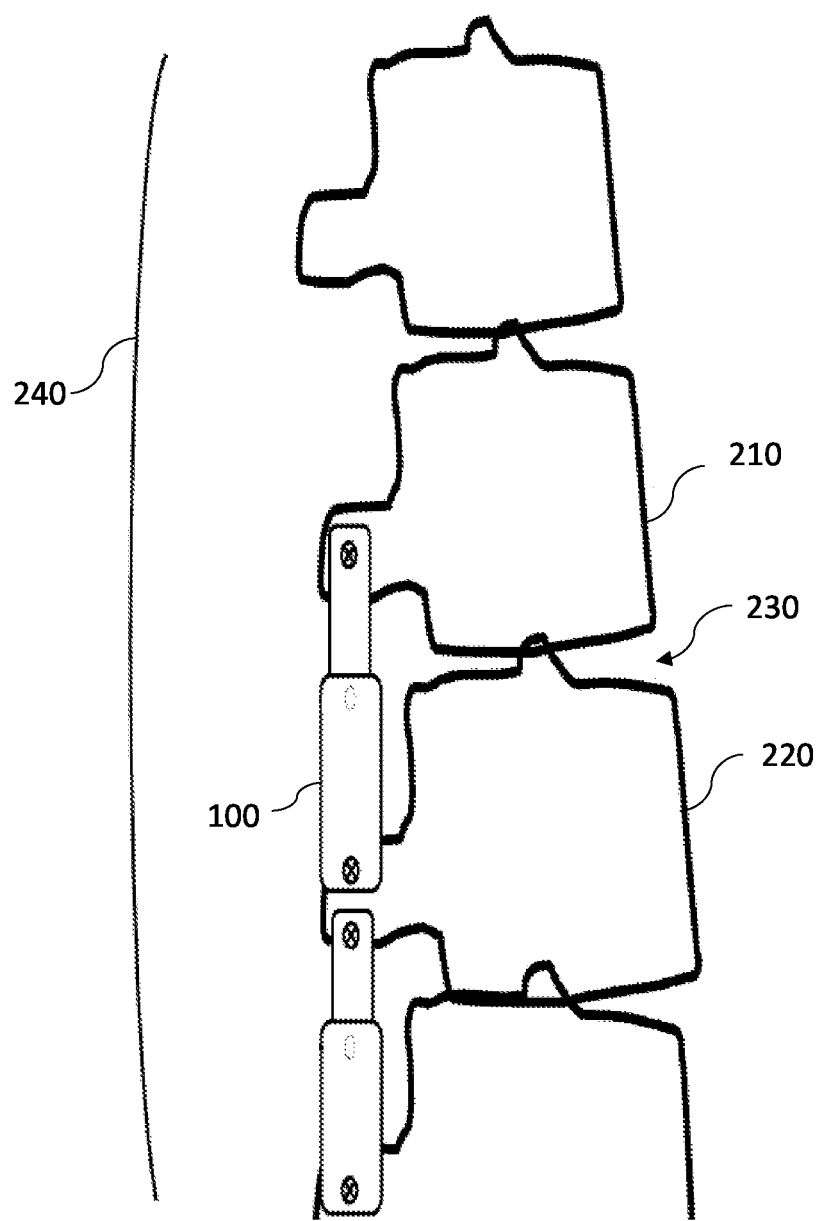
FIG. 7 depicts the readjustment of the spacing between vertebral bones, according to an exemplary embodiment of the present invention.

FIG. 3 shows the target spine curvature and inter-vertebrae space adjusted during the surgery. Upon aligning the vertebrae, the fasteners can be engaged, and the surgery can be finished. The disclosed spinal stabilization device 100 can keep the spacing constant between the spinal bones. FIG. 4 shows, the after surgery, the skin joined, and the fasteners of the spinal stabilization device 100 engaged and the spacing of the spine bones remains fixed. Referring to FIG. 5, which shows the vertebrae as in FIG. 4 while the patient recovers and can move freely. The alignment of the vertebrae is in a fixed position by the implanted spinal stabilization device 100. However, over time as the patient engages in normal activities, the spinal alignment may change. The positions of the vertebral bones may need to be readjusted to restore the desired spacing between the adjacent vertebral bones. FIG. 6 shows the vertebral bones 210 and 220 slightly disoriented and the spacing between the vertebral bones 210 and 220 is different from the one shown in FIG. 5. To readjust the vertebral bones, invasive surgery to gain access to the vertebral bones may not be desired. The disclosed spinal stabilization device 100 allows adjusting the vertebral bones without an incision in the skin and without invasive surgery. It is understood that both spacing between the bones and the angle between the bones i.e., curvature can be adjusted. The device further includes a casing mounted to the outer tubes and can encase the fastener. The casing can be configured such as the fastener can be extended and retracted from the holes of the outer tube and the inner tube, thus locking and unlocking the inner tube respectfully. An external field of energy in form of magnetic field, ultrasound field, and like can be applied to create the necessary force needed to extend or retract the fastener. The external field thus can create a mechanical force to engage and disengage the fastener. The fastener includes a pin that can be inserted into the holes of the inner tube and the outer tube. FIG. 6 shows two transmitters 610 that can generate a focused magnetic field.

In one embodiment, the fastener can be a magnetized pin having a north pole and a south pole. The casing can include a spring mechanism to force the pins in an engaged position interlocking the inner tube to the outer tube. Magnetic field can be applied wherein the polarity of the magnetically generated force can be selected such as to engage or disengage the pins. For example, the magnetic force can be repulsive relative to the magnetized pins for engaging the pins and the magnetic force can be attractive relative to the magnetized pins for disengaging or pulling the pins out of the holes. The extent of the magnetic field required to actuate the magnetized pins can depend upon the number of magnetized pins. The more the number of the magnetized pins are for interlocking the inner tube, the greater the extent of the magnetic force may be required. Preferably, the extent the magnetic field can be limited to prevent any undesired effects such as unwanted disengagement of a pin, and moreover, the magnetic field can be focused. For example, the too strong external magnetic field can disturb other fasteners or structures that may not be desired. Moreover, this focus (or multiple focal points) needs to track the movements of the pins due to the patient's body. These movements can be created by maneuvers to correct the vertebral spacing and orientation. In one embodiment, a separate source of energy for each pin can be used, or beamforming can be used to create multiple focal points. In either case, tracking the pin or fastener location(s) affected by the body's motion may be recommended. In one case, creating a large external energy field to encompass the whole area (as opposed to having multiple focal points) may not be the optimum solution as it may be desirable to reposition only one implanted device. For example, to avoid disturbing or disengaging other implanted devices. Having a large energy field may disengage all pins/fasteners, creating undesired displacements. In one embodiment, while the external magnetic force is continued to be applied, the magnetized pins remain retracted in the fastener casing. Upon turning off the external magnetic force, the pins can extend through the holes in the outer tube into the holes of the inner tube resulting in the interlocking of the inner tube. The external magnetic field can be turned off once the vertebral bones could be readjusted i.e., once the repositioning of the vertebrae is done by the caretaker team, the external magnetic field can be switched off, allowing for the pin or fastener to go back to its locking position under the push-back (or pull-back) force exerted by the spring of the fastener casing. Another embodiment is to reverse the direction (or polarity) of the magnetic field to reengage the pin.

Adjusting the positioning of the vertebral structure non-invasively may be performed by a sequence of precise body movements under imaging techniques, such as fluoroscopy, using external and physical manipulations (i.e., maneuvers) of the patient. A multi-axial bed with straps attached to limbs/trunk/neck is also envisioned. In one exemplary embodiment, the patient can be subjected to a body position so as to create the least amount of stress on the retaining pins (to facilitate their disengagement). Also envisioned are the pins to have a small, embedded pressure sensors that could be interrogated via Radio Frequency Identification (RFID). The source of energy, such as magnetic, ultrasound, and the like, can then be focused on the retaining pin(s). Imaging techniques and pressure sensor data can be used to confirm disengagement of the pin. Then the patient can be subjected to predetermined maneuvers, movements, postures, and/or body positions, while the patient may lie on a multi-axial bed. In one embodiment, the patient may be instructed to get into a specific position or posture by moving the spine, trunk, head, neck, limbs. In certain embodiments, the care taking team may manually move the patient's body/limbs in and between different target positions. The multi-axial bed and straps can be adjusted to place the spine in the target position. The position of the vertebral bones and thus the vertebrae can be monitored by imaging techniques, such as fluoroscopy. Once, the desired positioning of the vertebral bones is achieved i.e., the desired spacing between the bones, the patient may be kept still and the fine body positioning adjustments can be done so that the holes of the outer tube and the inner tube can be aligned. Thereafter, the source of energy can be turned off to reengage the retaining pins. Very fine body positioning adjustments can be made to ensure the pins are fully engaged. The engagement of the pins can be verified by the pressure sensor data and fluoroscopy imaging. Once completed, the patient can be gently repositioned to a normal position. It is understood that alternatively to turning off the energy source, the energy source can be used to engage the fasteners as well. For example, the polarity of the magnetic source can be reversed to engage the pins. Also, it is understood that the fastener casing can include any other mechanism for effecting engagement and disengagements of the fasteners, the fasteners include pins, and one or more than one fastener can be simultaneously engaged and disengaged. In one case, the fasteners can be actuated by micro-actuators embedded in the fastener casing (not shown in the figures). The micro-actuators can be controlled wirelessly from outside the body. Moreover, the micro-actuators can be energized from an external source using the energy transmitted through the tissues. For example, the external source of energy can be an ultrasonic wave generator.

In one exemplary embodiment, the disclosed spinal stabilization device may allow post-operative readjustment of the spacing between the vertebrae and the angle of the curvature multiple times in a non-invasive manner and while the patient remains awake. After the initial implant and completion of the surgery, during the post-operative period and under well-defined postures and while the patient is fully awake, the position of the pins can be fine adjusted. To this end, first the at least one pin can be disengaged. Then, the patient can be physically subjected to very specific positions and when the optimum spinal shape is achieved, at least one pin is reengaged again. The engagement and disengagement of the pin can be controlled from outside the body hence does not necessitate any incision in the body. The engagement and disengagement of a pin can be implemented by embedded micro-actuators which are energized from outside the body. Alternatively, an energy field, such as a magnetic field can be used to create sufficient attractive/repulsive force to move the pin or pins. As such, the position of at least one pin defines the relative distance of the telescopic arms hence the spacing between the vertebrae and the angle of the curvatures can be readjusted multiple times and over a long period.

Figure 8:
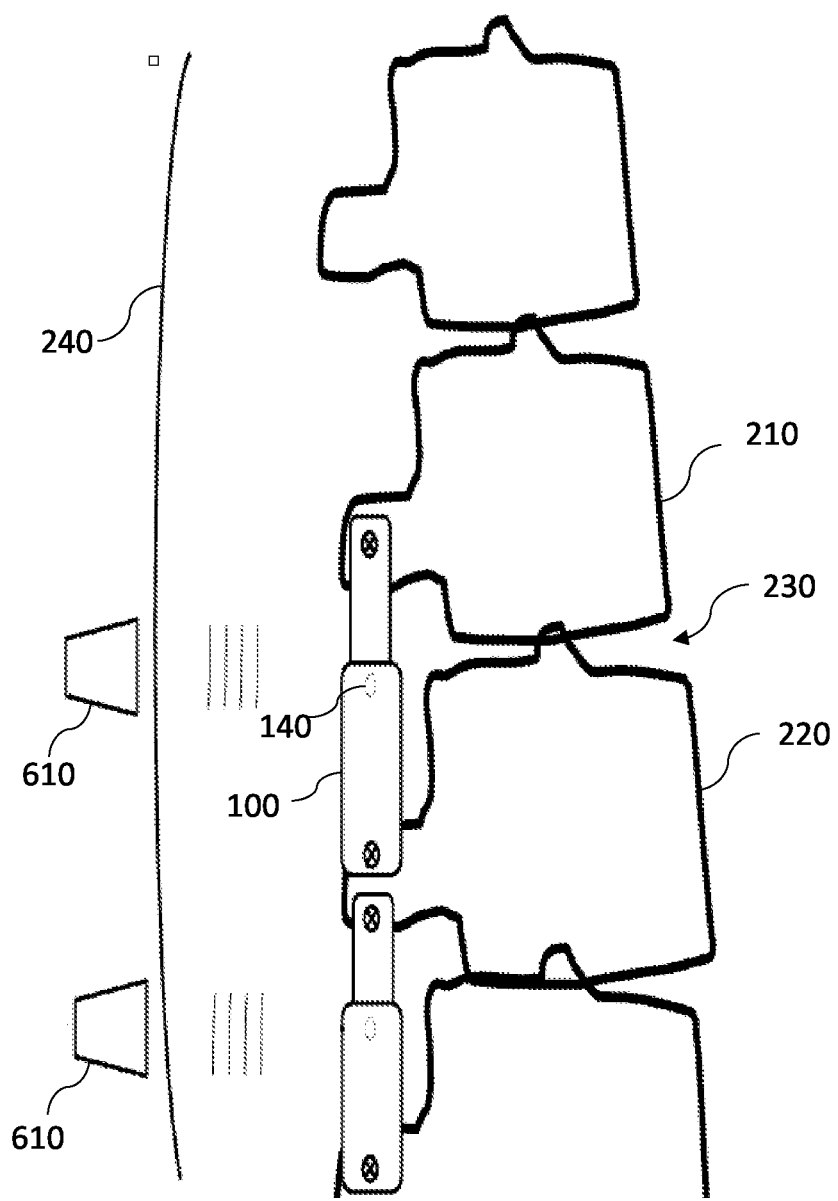
FIG. 8 depicts the application of the external magnetic field to re-engage the pins locking the movement of the inner tube relative to the outer tube after readjustment of the spaces as shown in FIG. 7, according to an exemplary embodiment of the present invention.
Figure 9:
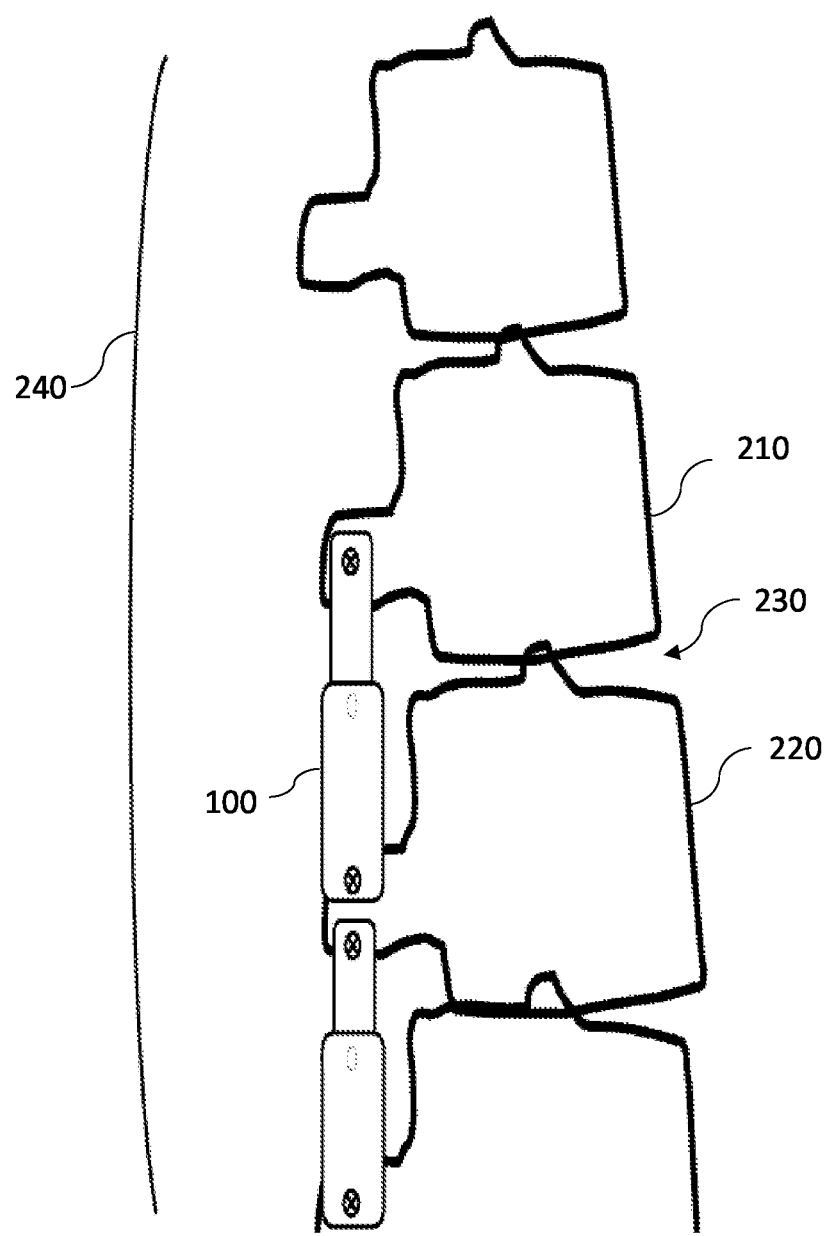
FIG. 9 shows the spacing between the vertebral bones after readjustment and healing, according to an exemplary embodiment of the present invention.

Referring to FIG. 8 which shows the reversal of the external magnetic source 610 resulting in engagement of the fastener 140. Once, pins 140 are engaged, the external magnetic source 610 can be removed, as shown in FIG. 9.

Figure 10:
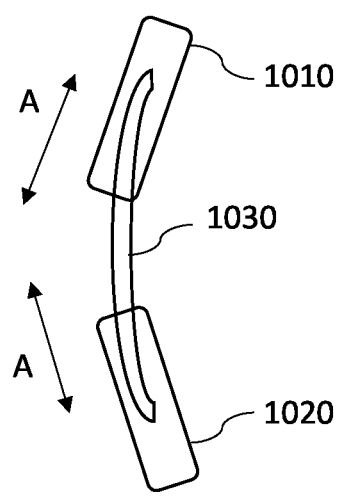
FIG. 10 depicts another exemplary embodiment of the spinal stabilization device, which is curved, according to the present invention.
Figure 11:
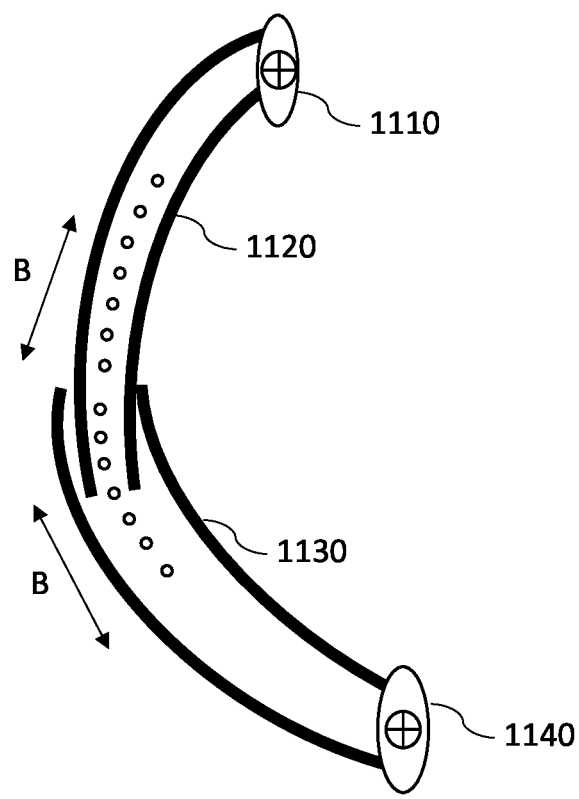
FIG. 11 shows another exemplary embodiment of the curved spinal stabilization device, according to the present invention.

FIG. 10 shows another exemplary embodiment of the disclosed spinal stabilization device 100 that is curved. FIG. 10 shows the two tubes i.e., the first tube 1010 and the second tube 1020, both are rigid. A curved bar 1030 interconnects the first tube 1010 and the second tube 1020. A groove or rail within the first tube 1010 and the second tube 1020 can guide the curved bar 1030, allowing for the adjustment of the two tubes. The length of the curved bar can be selected based on the anatomical dimensions of the patient, whereas the spacing between the two tubes can be adjustable (between a minimum and approximately the length of the curved bar). The same pin engagement/disengagement mechanism as the non-curved (straight) telescopic tubes can be employed to allow free movement between the two tubes and the curved bar, therefore non-invasive readjustment of the relative position after surgery (i.e., in-situ) is possible, without the need to open the body (tissue structures). In FIG. 10, the directions of the arrow "A" show how much change the positions of the tubes can undergo. It is understood that the extent to which the movement may occur has been exaggerated. Indeed, so much displacement range may not be required for this application. FIG. 11 shows another implementation of the curved tubes as shown in FIG. 10. The spinal stabilization device can include an inner tube 1120 and an outer tube 1130. Both the inner tube and the outer tube can be curved wherein the degree of curve can be proportional to the curvature of the spine. An end of the inner tube can have a first bone pedicle 1110 and an end of the outer tube can have the second bone pedicle 1140.

In one exemplary embodiment, it is envisioned a sandwich-type of construction for the casings. The spinal stabilization device having the two rigid parts, wherein the two rigid parts can be coupled using a material that becomes soft/malleable under application of an external energy field (such as magnetic or ultrasound). Once soft (hence malleable), the spacing between the two vertebrae can be adjusted and after the optimum spacing being reached, the external source of energy to be removed. Upon removing the external energy field, material can solidify back locking the vertebrae in place. In this embodiment, the two pedicle screws can fasten the rigid casings to the vertebrae, and the interlocking fasteners or pins may not be needed. One advantage is that the holes where the pins need to fit in cannot be filled/disturbed with debris/tissue growth, hence increasing the longevity of the system.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A spinal stabilization device comprising:
an outer tube, the outer tube has a proximal end and a distal end, a plurality of holes in the outer tube between the proximal end and the distal end;
an inner tube, the inner tube has a proximal end and a distal end, a plurality of holes in the inner tube between the proximal end and the distal end, the proximal end of the inner tube slidably inserted into the distal end of the outer tube;
at least one fastener configured to be inserted through a hole of the plurality of holes of the outer tube into a hole of the plurality of holes of the inner tube for interlocking the inner tube and the outer tube;
at least one casing comprising the at least one fastener, wherein the at least one casing is mounted to the outer tube adjacent to the hole of the outer tube, wherein the at least one fastener and the at least one casing are configured such as the at least one fastener can be triggered non-invasively from outside a body, in which the spinal stabilization device is implanted, to be engaged and disengaged, wherein the at least one fastener interlocks the inner tube and outer tube when engaged and unlock the inner tube and the outer tube when disengaged;

at least one first pedicle screw configured in the distal end of the inner tube; and at least one second pedicle screw configured in the proximal end of the outer tube, wherein the at least one first pedicle screw and the at least one second pedicle screw are configured to fasten to at least two vertebral bones.

2. The spinal stabilization device according to claim 1, wherein the at least one fastener is a magnetized pin, and the magnetized pin is configured to be inserted into respective holes of the inner tube and the outer tube for interlocking the inner tube and the outer tube by an application of an external magnetic field and retracted from the respective holes by the application of the external magnetic field.

3. The spinal stabilization device according to claim 2, wherein the magnetized pin is inserted on the application of the external magnetic field of a first polarity and the magnetized pin is retracted on the application of the external magnetic field of a second polarity, wherein the second polarity is reverse of the first polarity.

4. The spinal stabilization device according to claim 2, wherein the at least one casing comprises a spring configured to push the magnetized pin, wherein the magnetized pin and the spring are configured to be retracted upon the application of the external magnetic field.

5. The spinal stabilization device according to claim 1, wherein the at least one fastener comprises two fasteners.

6. The spinal stabilization device according to claim 5, wherein the two fasteners are magnetized pins.

7. The spinal stabilization device according to claim 1, wherein the at least one casing comprises a micro-actuator, the micro-actuator configured to cause the at least one fastener to be engaged and disengaged, wherein the micro-actuator is configured to be driven by an external ultrasonic wave generator.

8. The system according to claim 1, wherein the spinal stabilization device further comprises a pressure sensor embedded to the magnetized pin, the pressure sensor is configured to be interrogated via Radio Frequency Identification (RFID), wherein a signal from the pressure sensor indicated disengagement of the magnetized pin.

9. The spinal stabilization device according to claim 1, wherein the inner tube and the outer tube are curved, wherein the degree of curve is proportional to curvature of spine.

10. A method for correcting a position of two or more vertebral bones in a body, the method comprising the steps of:
implanting a spinal stabilization device, wherein the spinal stabilization device comprises:
an outer tube, the outer tube has a proximal end and a distal end, a plurality of holes in the outer tube between the proximal end and the distal end,
an inner tube, the inner tube has a proximal end and a distal end, a plurality of holes in the inner tube between the proximal end and the distal end, the proximal end of the inner tube slidably inserted into the distal end of the outer tube,
at least one fastener configured to be inserted through a hole of the plurality of holes of the outer tube into a hole of the plurality of holes of the inner tube for interlocking the inner tube and the outer tube,
at least one casing comprising the at least one fastener, wherein the at least one casing is mounted to the outer tube adjacent to the hole of the outer tube, wherein the at least one fastener and the at least one casing are configured such as the at least one fastener can be triggered non-invasively from outside the body to be engaged and disengaged, wherein the at least one fastener interlocks the inner tube and outer tube when engaged and unlock the inner tube and the outer tube when disengaged,
at least one first pedicle screw configured in the distal end of the inner tube, and
at least one second pedicle screw configured in the proximal end of the outer tube,
wherein the at least one first pedicle screw is fastened to at least a first vertebral bone and the at least one second pedicle screw is fastened to at least a second vertebral bone;
applying, non-invasively, from an external source, a force or a signal to cause the at least one fastener to disengage resulting in unlocking of the inner tube and the outer tube;
upon disengaging, repositioning, non-invasively, the at least first vertebral bone and the at least second vertebral bone;
upon repositioning, non-invasively reengaging the at least one fastener to interlock the inner tube and outer tube.

11. The method according to claim 10, wherein the step of repositioning further comprises subjecting the body to a set of predetermined body movements and postures.

12. The method according to claim 11, wherein the method further comprises the steps of:
imaging the implanted spinal stabilization device to guide the steps of the disengaging of the at least one fastener, the repositioning, and the reengaging.

13. The method according to claim 10, wherein the at least one fastener is a magnetized pin, and the magnetized pin is configured to be inserted into respective holes of the inner tube and the outer tube for interlocking the inner tube and the outer tube by an application of an external magnetic field and retracted from the respective holes by the application of the external magnetic field.

14. The method according to claim 13, wherein the step of applying the force further comprises applying the external magnetic field of a first polarity to attract the magnetized pin causing retraction, and wherein the step of inserting the at least one fastener further comprises the steps of applying the external magnetic field of a second polarity to repel the magnetized pin.

15. The method according to claim 13, wherein the at least one casing further comprises a spring configured to push the magnetized pin, wherein method further comprises the step of:
applying the external magnetic field to the magnetized pin resulting in retraction of magnetized pin, wherein the external magnetic field is continued to be applied during the step of repositioning, and
turning off the external magnetic field to release the magnetized pin for reengaging.

16. The method according to claim 13, wherein the external magnetic field is beamformed to the respective magnetic pin.

17. The method according to claim 10, wherein the at least one casing comprises a micro-actuator, wherein the method further comprises the steps of:
sending non-invasively, from the external source, the signal to the micro-actuator causing the at least one fastener to disengage.

* * * * *